United States Patent [19]

Ahrens et al.

[11] Patent Number: 5,025,016
[45] Date of Patent: Jun. 18, 1991

[54] PYRIMIDINE-THIOALKYL PYRIDINE DERIVATIVES, MEDICAMENTS CONTAINING THESE COMPOUNDS, AND METHOD OF TREATMENT

[75] Inventors: Kurt H. Ahrens, Nuremberg; Helmut Schickaneder, Eckental; Heidrun Engler, Cadolzburg; Istvan Szeleny, Schwaig, all of Fed. Rep. of Germany

[73] Assignee: Ludwig Heumann & Co. GmbH, Nuremberg, Fed. Rep. of Germany

[21] Appl. No.: 248,927

[22] Filed: Sep. 26, 1988

Related U.S. Application Data

[60] Division of Ser. No. 16,564, Feb. 19, 1987, abandoned, which is a continuation of Ser. No. 605,926, May 1, 1984, abandoned.

[30] Foreign Application Priority Data

May 5, 1983 [DE] Fed. Rep. of
Germany ...................... 83104452[U]

[51] Int. Cl.$^5$ .................. A61K 31/505; C07D 401/00; C07D 403/00; C07D 239/02
[52] U.S. Cl. .................................... 514/274; 544/300; 544/310; 544/316; 544/317
[58] Field of Search ............... 544/300, 310, 316, 317; 514/274

[56] References Cited

U.S. PATENT DOCUMENTS 4,866,066 9/1989 Schickaneder et al. ............ 544/300

FOREIGN PATENT DOCUMENTS 1213279 10/1986 Canada ............................... 544/300
1881/83 4/1983 Denmark ........................... 544/300

Primary Examiner—Mary C. Lee
Assistant Examiner—Robert C. Whittenbaugh
Attorney, Agent, or Firm—Burns, Doane, Swecker & Mathis

[57] ABSTRACT

The invention relates to pyrimidine-thioalkyl pyridine derivatives corresponding to the following general formula

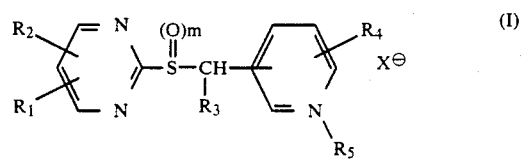

in which $R_1$ to $R_4$, independently of one another, represent hydrogen, lower alkyl, halogen, amino or hydroxy groups, $R_5$ represents a free electron pair or a lower alkyl group, a halogen atom, m has the value 0 or 1, the pyrimidine-thioalkyl group being bonded in the 2-, 3- or 4-position of the pyridine ring, and to therapeutically compatible acid addition salts thereof. The invention also relates to a process for producing the new pyrimidine-thioalkyl pyridine derivatives and to medicaments containing these compounds.

32 Claims, No Drawings

PYRIMIDINE-THIOALKYL PYRIDINE DERIVATIVES, MEDICAMENTS CONTAINING THESE COMPOUNDS, AND METHOD OF TREATMENT

This application is a divisional, of application Ser. No. 07/016,564, filed Feb. 19, 1987, now abandoned in turn a continuation of Ser. No. 06/605,926, filed May 1, 1984 now abandoned.

This invention relates to new pyrimidine-thioalkyl pyridine derivatives, a process for their production and to medicaments containing these compounds.

The new compounds according to the invention are surprisingly distinguished by high bronchosecretolytic and mucolytic activity and by antiphlogistic activity which are of therapeutic value.

It is known that reducing the viscosity of sputum by medicaments is an important therapeutic objective in the treatment of acute and chronic bronchial illnesses (for example infections of the respiratory tract, asthmatic complaints, obstructive disorders and the like). There are different types of medicaments for treating these illnesses, differing in their local and systemic activity. The locally active types include inter alia N-acetyl cysteine, whilst the systemic types include, for example, ambroxol, i.e. trans-4-(2-amino-3,5-dibromobenzyl)-aminocyclohexanol, an established bronchosecretolytic in the treatment of bronchial illness. This compound is described, for example, in DE-PS 1 593 579.

The object of the present invention is to provide new bronchosecretolytic and mucolytic compounds of which the oral and parenteral effectiveness is considerably improved over that of compounds which are known to act favorably in the same direction, such as ambroxol for example.

This object is achieved by the present invention.

Accordingly, the present invention relates to new pyrimidine-thioalkyl pyridine derivatives corresponding to the following general formula

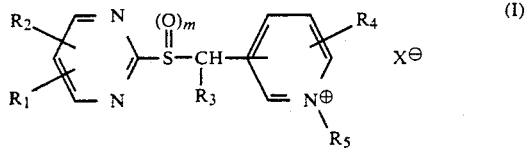

in which $R_1$ to $R_4$, independently of one another, represent hydrogen, lower alkyl, halogen, amino or hydroxy groups, $R_5$ represents a free electron pair or a lower alkyl group, X is a halogen atom where $R_5$ is a lower alkyl group, m=0 or 1, the pyrimidine-thioalkyl group being bonded in the 2-, 3- or 4-position of the pyridine ring, and therapeutically compatible acid addition salts thereof.

In general formula I, $R_1$ and $R_2$ independently of one another represent, in particular, hydrogen atoms, lower alkyl, amino or hydroxy groups. Lower alkyl groups are straight-chain or branched-chain alkyl groups containing from 1 to 4 carbon atoms, such as for example methyl groups, ethyl groups, isopropyl groups and butyl groups, preferably methyl groups. When one of the substituents $R_1$ and $R_2$ is a hydrogen atom, the other group is bonded to the pyrimidine ring in the 4- or 5-position or in the 5- or 6-position, in which case the 4-position is preferred for $R_1$ and the 6-position for $R_2$. When both the groups $R_1$ and $R_2$ are radicals other than hydrogen atoms, they may be in the 4-5-, 5-6- or 4-6-position, the 4-6-position being preferred.

In general formula I, $R_3$ represents in particular a hydrogen atom or a lower alkyl group (as defined above), preferably a methyl group.

$R_4$ is in particular a hydrogen atom, a halogen atom or a lower alkyl group (as defined above). Halogen atoms are, for example, fluorine atoms, chlorine atoms, bromine atoms and iodine atoms, preferably chlorine atoms.

Depending on the substitution of the pyrimidinethioalkyl group (formula Ia), $R_4$ may be bonded in the 2,3,4,5 and 6 positions of the pyridine ring (i.e. in the o-, m- or p-position to the nitrogen atom), the 2- and 6-position (i.e. the o-position) being preferred.

In general formula I, $R_5$ represents a free electron pair or a lower alkyl group (as defined above), preferably a methyl or ethyl group. Where $R_5$ represents an alkyl group, X represents a halogen atom, such as for example a chlorine, bromine or iodine atom, preferably an iodine atom.

In general formula I, m has the value 0 or 1. As defined above, the pyrimidine-thioalkyl group corresponding to the following general formula

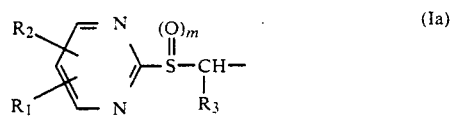

may be bonded in the 2-, 3- or 4-position of the pyridine ring, the 3-position being preferred.

The compounds corresponding to general formula I ($R_3$=H, m=0, $R_5$=free electron pair) may exist in various tautomeric forms, such as for example:

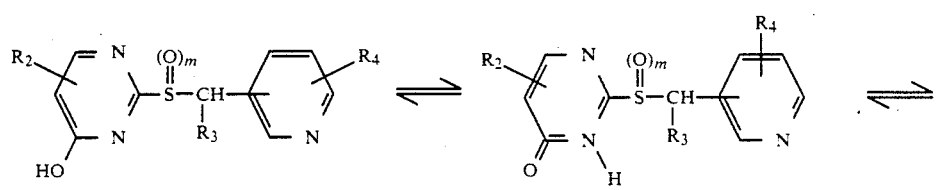

-continued

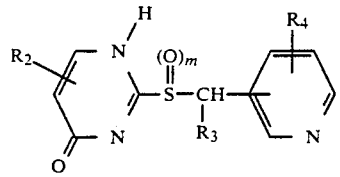

In addition, in cases where $R_3$ represents alkyl, m has the value O and where $R_3$ represents hydrogen and m has the value 1, the compounds corresponding to general formula I may exist as racemates which may be split into their enantiomers by suitable chiral reagents, such as for example optically active tartaric acid.

Where $R_3$ represents alkyl and m has the value 1, the compounds corresponding to general formula I may exist as diastereomer pairs which, if desired, may be split into the diastereomers by fractional crystallization. Accordingly, the compounds according to the invention also include all these above-mentioned isomeric forms.

The compounds corresponding to general formula I readily form acid addition salts, for example mono-, di- and tri-addition salts, such as for example hydrochlorides, hydrobromides, sulfates, acetates, maleinates, maleates, fumarates, oxalates, methane sulfonates, tartrates, citrates, succinates and embonates, etc.

The compounds according to the invention (m=0 and $R_5$=free electron pair) may be produced by a process which is characterized in that a thiolate corresponding to the following general formula

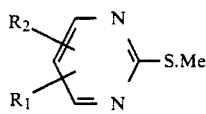

(II)

in which $R_1$ and $R_2$ are as defined above and Me is an alkali atom, is reacted in known manner with a picolyl chloride hydrohalide corresponding to the following general formula

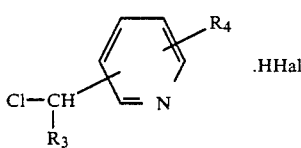

(III)

in which Hal is a halogen atom and in which the chloromethyl group is in the 2-, 3- or 4-position of the pyridine ring and $R_3$ and $R_4$ are as defined above, in an aqueous-alcoholic alkali hydroxide solution containing the alkali hydroxide in anexcess over and above the stoichiometric quantity, to form a compound corresponding to the following general formula

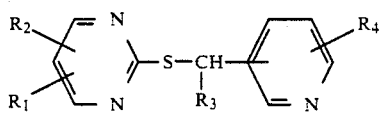

(IV)

and in that the free base thus obtained is optionally converted into a therapeutically compatible acid addition salt.

In formula II, Me is an alkali atom, for example a potassium or sodium atom, preferably a sodium atom.

In general formula III, Hal is a halogen atom, for example a chlorine or bromine atom, preferably a chlorine atom. the reaction is carried out in an aqueous-alcoholic alkali hydroxide solution in which the alkali hydroxide is present in an excess over and above the stoichiometric quantity, preferably in at least twice the equimolar quantity. The aqueous-alcoholic solution used is preferably an aqueous-ethanolic solution. Sodium hydroxide is preferably used as the alkali hydroxide. The reaction is best carried out by dissolving the thiolate corresponding to general formula II in the aqueous- alcoholic alkali hydroxide solution at 0° to 5° C. and reacting the resulting solution for 2 to 6 hours, preferably for 4 hours, at room temperature with an equimolar quantity of the picolyl chloride-hydrohalide compound dissolved in aqueous-alcoholic, preferably aqueous-ethanolic, solution.

Because the alkali hydroxide is used in a stoichiometric excess, the free base is obtained and may subsequently be converted into a therapeutically compatible salt in the usual way by reaction with a pharmaceutically acceptable acid.

The other compounds according to the invention (m=1 and $R_5$=free electron pair) may be produced by a process which is characterized in that a compound corresponding to the following general formula

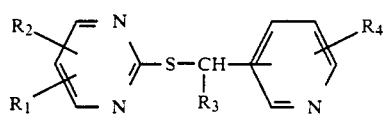

(IV)

in which $R_1$, $R_2$, $R_3$ and $R_4$ are as defined above, is reacted in known manner with an equimolar quantity of an oxidizing agent, for example potassium permanganate, hydrogen peroxide or m-chloroperbenzoic acid, preferably m-chloroperbenzoic acid, in inert solvents, such as halogenated hydrocarbons, preferably methylene chloride. The reaction is carried out at 20° to 30° C. and preferably at 25° C. by adding an equimolar quantity of m-chloroperbenzoic acid dissolved in methylene chloride dropwise over a period of 10 to 15 minutes. Working up of the reaction solution and isolation of the compounds corresponding to the following general formula

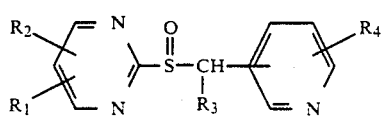

(V)

are carried out in the usual way. The free base obtained is then converted into a therapeutically compatible salt with a pharmaceutically acceptable acid in the same way as described above.

The other compounds according to the invention (m=O, $R_5$=lower alkyl, X=halogen) may be produced by a process which is characterized in that an equimolar quantity of an alkyl halide, preferably an alkyl iodide, is added in known manner to a compound corresponding to the following general formula

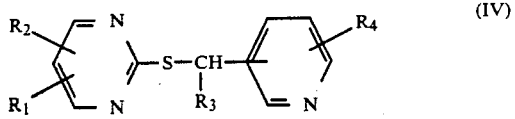
(IV)

in which $R_1$, $R_2$, $R_3$ and $R_4$ are as defined above, in acetone and the two reactants left to react for 1 hour at reflux temperature. The compound corresponding to the following general formula

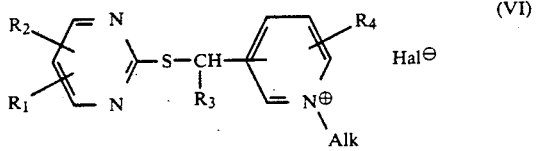
(VI)

in which $R_1$ to $R_5$, m and X are as defined above, is isolated by concentrating the reaction solution and crystallizing the product formed in an alcoholic solvent, preferably in isopropanol.

The compounds according to the invention are distinguished by surprisingly improved bronchosecretolytic and mucolytic activity so that they may be administered in considerably smaller quantities for therapy than known compounds. In addition, the compounds according to the invention were found to show antiphlogistic activity.

For example, compounds corresponding to general formula I, in which $R_1$ is a hydroxy group bonded in the 4-position of the pyrimidine ring, $R_2$ is a hydrogen atom or $R_1$ and $R_2$ each represent an amino group bonded in the 4- and 6-positions of the pyrimidine ring, $R_3$ and $R_4$ each represent a hydrogen atom, $R_5$ represents a free electron pair and m has a value O, the pyrimidine-thioalkyl group being bonded in the 3-position of the pyridine ring, show antiphlogistic activity. Accordingly, these compounds could be considered for use as antiphlogistic, i.e. inflammation-preventing, agents.

Accordingly, the present invention also relates to a pharmaceutical preparation or a medicament showing bronchosecretolytic and mucolytic activity which, in addition to standard auxiliaries and excipients, contains at least one pyrimidine-thioalkyl pyridine derivative corresponding to general formula I.

The pharmaceutical preparation according to the invention may be used for treating all types of brochial illness, for example acute and chronic respiratory diseases, for post-operative treatment of the respiratory tracts and in any process where it is desirable to liquefy the bronchial mucus.

The compound used in accordance with the invention is preferably orally administered. The oral daily dose is usually from 0.01 to 0.2 g and preferably from 0.02 to 0.1 g which may be administered in one or more daily doses.

In individual cases, it may be necessary to deviate from the doses indicated, depending on the reaction of the individual to the active principle or to the nature of its formulation and upon the time at which or intervals at which the active principle is administered. For example, there are cases where less than the minimum dose indicated above may be sufficient, whereas in other cases the upper limit indicated above has to be exceeded. Where relatively large quantities have to be administered, it may be advisable to divide them into several individual doses spread over 24 hours.

For oral administration, the active principle may be formulated for example in the form of capsules which may be prepared by conventional methods using pharmaceutically acceptable excipients, for example binders (such as pregelatinized cornstarch, polyvinyl pyrrolidone or hydroxypropyl methyl cellulose); fillers (such as lactose, microcystalline cellulose or calcium phosphate); lubricants (such as magnesium stearate, talcum or silica); disintegrating agents (for example potato starch or sodium starch glycolate); or moistening agents (for example sodium lauryl sulfate). The capsules may be coated by known methods. Liquid preparations for oral administration or for direct instillation may be formulated, for example, as solutions, syrups or suspensions or, alternatively, may be presented as a dry product for reconstitution before use either with water or with any other suitable vehicle. Liquid preparations such as these may be prepared by conventional methods using pharmaceutically acceptable additives, for example suspending agents (such as sorbitol syrup, methyl cellulose or hydrogenated edible fats); emulsifiers (for example lecithin or acacia); non-aqueous vehicles (for example almond oil, oily esters or ethyl alcohol); and preservatives (for example methyl- or propyl-p-hydroxybenzoates or sorbic acid).

For buccal administration, the preparations may be presented in the form of tablets or lozenges formulated in the usual way.

The compounds used in accordance with the invention may be formulated for parenteral administration by injection or for infusion. Preparations for injection may be presented in unit dose form, for example in ampoules or in multiple-dose containers, with an added preservative. The preparations may also assume such forms as suspensions, solutions or emulsions in oily or aqueous vehicles, and may contain formulation aids, such as suspension agents, stabilizers and/or dispersants.

Alternatively, the active principle may even assume the form of a powder for reconstitution before use with a suitable vehicle, for example sterile, pyrogenfree water.

For administration by inhalation, the compound used in accordance with the invention is suitably released in the form of an aerosol spray from pressurized packs or atomizers using a suitable propellent, for example dichlorodifluoromethane, trichlorofluoromethane, dichlorotetrafluoroethane, carbon dioxide or any other suitable gas. In the case of a pressurized aerosol, the dose unit may be determined by the provision of a valve for dispensing a measured quantity.

Pharmacological studies have shown that the pyrimidinethioalkyl pyridine derivatives used in accordance with the invention are superior in their bronchosecretolytic and mucolytic properties to the known comparison product, ambroxol. More particularly, the following studies were carried out.

1. PHARMACODYNAMICS

1.1 Secretion-stimulating activity

Bronchosecretolytic compounds promote the tracheal secretion of phenol red (Chronic Bronchitis Research Group, Chinese Medical Journal 3: 259, 1977).

The increase in the tracheal secretion of phenol red is a measure of bronchosecretolytic activity. This activity of the test substances was investigated after oral administration to female mice. The $ED_{50}$-values shown in Table 1 were calculated from the regression curves.

TABLE I

| Compound | $ED_{50}$ (mg/kg) |
|---|---|
| Ambroxol | 250 |
| Example 1 | 5 |
| Example 2 | 100 |
| Example 3 | 2 |
| Example 4 | >100 |
| Example 5 | 15 |
| Example 6 | 2 |
| Example 7 | 15 |
| Example 8 | >100 |
| Example 9 | 2 |
| Example 10 | 100 |
| Example 11 | 10 |
| Example 12 | 1 |
| Example 13 | 70 |

1.2 Antiphlogistic activity

The antiphlogistic properties of the compounds according to the invention were determined by the carrageenin-oedema test in male rats (average weight 130–160 g, SIV 50, Messrs Ivanovas, Kisslegg). The inhibition of the carrageenin-induced inflammation (oedema formation) was measured on the right-hand rear paw. The test substances were administered intragastrally by esophagus probe 30 minutes before injection of the carrageenin. The results are shown in Table II (Higgs et.al., European Journal of Pharmacology 66, 81–86 (1980)).

TABLE II

| Compound | Dose mg/kg i.g. | Inhibition in % |
|---|---|---|
| Example 2 | 100 | 45 |
| Example 4 | 100 | 30 |

The invention is illustrated by the following examples.

EXAMPLE 1

Production of 4-amino-2-(pyridyl-3-methylthio)-pyrimidine

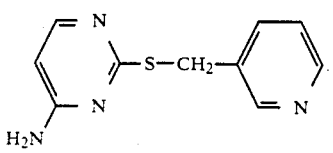

8.4 g (0.21 mole) of sodium hydroxide dissolved in 120 ml of water are added dropwise at 0° C. to a solution of 12.7 g (0.1 mole) of 4-amino-2-mercaptopyrimidine in 250 ml of ethanol. 16.4 g (0.1 mole) of 3-picolyl chloride hydrochloride dissolved in 100 ml of water are then slowly added, followed by stirring for 4 hours at room temperature. The reaction solution is concentrated, taken up in 500 ml of ether, the organic phase washed three times with 100 ml of water, dried over sodium sulfate, filtered off and the filtrate concentrated in vacuo. The solid accumulating is recrystallized from ethyl acetate.

Colorless crystals melting at 119–120° C.
Rf = 0.40 (CH$_2$Cl$_2$/MeOH 9:1)
Yield: 12.4 g (57%)
C$_{10}$H$_{10}$N$_4$S (218)   Calculated: C 55.03  H 4.62  N 25.67
                               Observed:   C 55.14  H 4.63  N 25.80
$^1$H-NMR-data:      δ = 4.33 (s) (S—C$\underline{H}_2$) 2 H,
(d$_6$-DMSO,              6.17 (d) (aromatic-$\underline{H}$) 1 H,
TMS as internal           7.00 (s) (—N$\underline{H}_2$, exchangeable for D$_2$O)
standard)                 2 H,
                          7.33 (dd) (aromatic-$\underline{H}$) 1 H,
                          7.83 (m) (aromatic-$\underline{H}$) 1 H,
                          7.93 (d) (aromatic-$\underline{H}$) 1 H,
                          8.43 (m) (aromatic-$\underline{H}$) 1 H,
                          8.67 (s) (aromatic-$\underline{H}$) 1 H ppm.

EXAMPLE 2

Production of 4-hydroxy-2-(pyridyl-3-methylthio)-pyrimidine

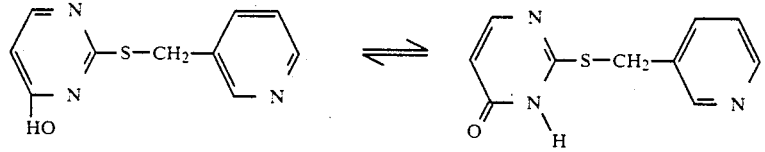

This compound is produced as in Example 1 from 4-hydroxy-2-mercaptopyrimidine and 3-picolyl chloride hydrochloride.

Colorless crystals melting at 167–168° C.
Rf = 0.31 (CH$_2$Cl$_2$/MeOH 9:1)
Yield: 6.8 g (32%)
C$_{10}$H$_9$N$_3$OS (213)   Calculated: C 54.78  H 4.14  N 19.16
                              Observed:   C 54.71  H 4.19  N 19.22
$^1$H-NMR-data:      δ = 4.47 (s) (—S—C$\underline{H}_2$) 2 H,
(d$_6$-DMSO, TMS as       6.17 (d) (aromatic-$\underline{H}$) 1 H,
internal standard)        7.37 (dd) (aromatic-$\underline{H}$) 1 H,
                          7.77–8.10 (m) (aromatic-H) 2 H,
                          8.50 (d) (aromatic-$\underline{H}$) 1 $\underline{H}$,
                          8.70 (s) (aromatic-$\underline{H}$) 1 H,
                          12.66 (s. broad) (—O$\underline{H}$) (exchangeable for D$_2$O) 1 H ppm.

EXAMPLE 3

Production of 4-amino-6-hydroxy-2-(pyridyl-3-methylthio)-pyrimidine

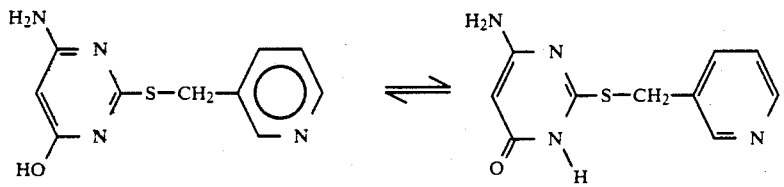

This compound is produced as in Example 1 from 4-amino-6hydroxy-2-mercaptopyrimidine and 3-pipolyl chloride hydrochloride.

Colorless crystals melting at 210–211° C.
Rf = 0.57 (CH$_2$Cl$_2$/MeOH 8:2)
Yield: 13.3 g (57%)
C$_{10}$H$_{10}$N$_4$OS (234)

| | Calculated: C 51.27 H 4.30 N 23.91 |
|---|---|
| | Observed: C 51.37 H 4.35 N 24.03 |
| $^1$H-NMR-data: (d$_6$-DMSO, TMS as internal standard) | δ = 4.37 (s) (S—C$\underline{H}_2$) 2 H, 5.03 (s) ( > = C$\underline{H}$) 1 H, 6.60 (s) (—N$\underline{H}_2$) (exchangeable for D$_2$O) 2 H, 7.33 (dd) (aromatic-$\underline{H}$) 1 H, 7.87 (d) (aromatic-$\underline{H}$) 1 H, 8.70 (s) (aromatic-$\underline{H}$) 1 H, 11.50 (s) (N—$\underline{H}$) (exchangeable for D$_2$O) 1 H ppm. |

EXAMPLE 4

Production of 4,6-diamino-2-(pyridyl-3-methylthio)-pyrimidine succinate

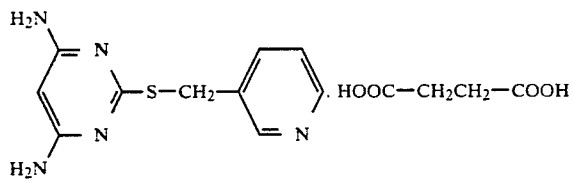

This compound is produced as in Example 1 from 4,6-diamino-2-meracptopyrimidine and 3-picolyl chloride hydrochlorde. The succinate is produced by adding to an ethanolic solution of 4,6-diamino-2-(pyridyl-3-methylthio)-pyrimidine an equimolar 10% solution of succinic acid in ethanol. The succinate accumulates in analytically pure form.

Colorless crystals melting at 149–150° C.
Rf = 0.22 (CH$_2$Cl$_2$/MeOH 95:5 NH$_3$-vapors)

Yield: 15.1 g (43%)
C$_{14}$H$_{17}$N$_5$O$_5$S (351)

| | Calculated: C 47.86 H 4.88 N 19.93 |
|---|---|
| | Observed: C 47.80 H 4.92 N 19.81 |
| $^1$H-NMR-data: (d$_6$-DMSO, TMS as internal standard) | δ = 2.43 (s) (—(C$\underline{H}_2$)$_2$—) 4 H 4.23 (s) (—S—C$\underline{H}_2$) 2 H, 5.20 (s) (aromatic-$\underline{H}$) 1 H, 6.13 (s) (2-N$\underline{H}_2$) (exchangeable for D$_2$O) 4 $\underline{H}$, 7.27 (dd) (aromatic-$\underline{H}$) 1 H, 7.83 (d) (aromatic-$\underline{H}$)1 H 8.43 (d) (aromatic-$\underline{H}$) 1 H, 8.67 (s) (aromatic-$\underline{H}$) 1 H, 12.20 (s, broad) (—COO$\underline{H}$) (exchangeable for D$_2$O) 2 $\underline{H}$ ppm. |

EXAMPLE 5

Production of 4-hydroxy-6-methyl-2-(pyridyl-3-methylthio)-pyrimidine

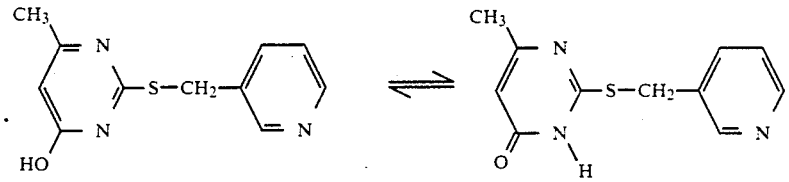

This compound is produced as in Example 1 from 4-hydroxy-6-methyl-2-mercaptopyrimidine and 3-picolyl chloride hydrochloride.

Colorless crystals melting at 168–169° C.
Rf = 0.41 (CH$_2$Cl$_2$/MeOH 9:1)
Yield: 15.8 g (68%)
C$_{11}$H$_{11}$N$_3$OS (233)

| | Calculated: C 56.63 H 4.75 N 18.01 |
|---|---|
| | Observed: C 56.69 H 4.89 N 17.99 |
| $^1$H-NMR-data: (d$_6$-DMSO, TMS as internal standard) | δ = 2.23 (s) (—C$\underline{H}_3$) 3 H, 4.43 (s) (S—C$\underline{H}_2$) 2 H. 6.07 (s) (aromatic-$\underline{H}$) 1 H. 7.40 (dd) (aromatic-$\underline{H}$) 1 H. 7.87 (m) (aromatic-$\underline{H}$) 1 H. 8.47 (d) (aromatic-$\underline{H}$) 1 H. 8.70 (s) (aromatic-$\underline{H}$) 1 H ppm. |

EXAMPLE 6

Production of 4-amino-6-hydroxy-2-(pyridyl-6-chloro-3-methylthio)-pyrimidine

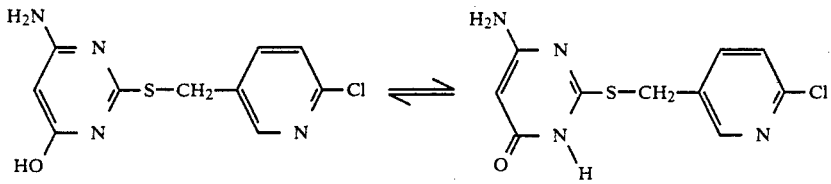

This compound is produced as in Example 1 from 4-amino-6-hydroxy-2-mercaptopyrimidine and 3-picolylchloride hydrochlorde.

Pale yellow crystals melting at 227–228° C.
Rf = 0.35 (CH$_2$Cl$_2$/MeOH 9:1)
Yield: 11.0 g (41%)
C$_{10}$H$_9$ClN$_4$OS (269)

| $^1$H-NMR-data: (d$_6$-DMSO, TMS as internal standard) | δ = 4.27 (s) (S—C$\underline{H}_2$) 2 H, 5.00 (s) (> = C$\underline{H}$) 1 H, 6.57 (s) (—N$\underline{H}_2$) (exchangeable for D$_2$O) 2 H, 7.43 (d) (aromatic-$\underline{H}$) 1 H, 7.97 (dd) (aromatic-$\underline{H}$) 1 H, 8.53 (s) (aromatic-$\underline{H}$) 1 H ppm. |
|---|---|

EXAMPLE 7

Production of 2-(pyridyl-3-(2-ethylthio)-pyrimidine oxalate

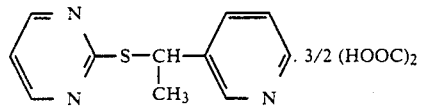

This compound is produced as in Example 1 from 2-mercaptopyrimidine and 3-(2-chloroethyl)-pyridine hydrochloride. The oxalate is produced as in Example 4.

Colorless crystals melting at 115–116° C.
Rf = 0.71 (CH$_2$Cl$_2$/MeOH 95:5 NH$_3$-vapors)
Yield: 10.9 g (31%)

| C$_{14}$H$_{14}$N$_3$O$_6$S (352) | Calculated: C 47.73 H 4.01 N 11.93 |
|---|---|
| | Observed: C 47.81 H 3.99 N 11.92 |
| $^1$H-NMR-data: (d$_6$-DMSO, TMS as internal standard) | δ = 1.77 (d) (—C$\underline{H}_3$) 3 H, 5.10 (q) (S—C$\underline{H}$) 1 H, 7.23 (t) (aromatic-$\underline{H}$) 1 H, 7.50 (dd) (aromatic-$\underline{H}$) 1 H, 8.07 (m) (aromatic-$\underline{H}$) 1 H, 8.43–8.93 (m) (aromatic-$\underline{H}$) 4 H ppm. |

EXAMPLE 8

Production of 2-(pyridyl-3-(2-ethylthio)-6-methyl-pyrimidine

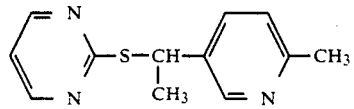

This compound is produced as in Example 1 from 2-mercaptopyrimidine and 3-(2-chloroethyl-6-methyl)-pyridine hydrochloride.

Pale yellow oil
Rf = 0.39 (CH$_2$Cl$_2$/MeOH 95:5)
Yield: 13.4 g (58%).
C$_{12}$H$_{13}$N$_3$S (231)

| $^1$H-NMR-data (CDCl$_3$, TMS as internal standard) | δ = 1.73 (d) (CH—C$\underline{H}_3$) 3 H, 2.50 (s) (—C$\underline{H}_3$) 3 H, 5.03 (q) (—C$\underline{H}$—CH$_3$) 1 H, 6.90 (t) (aromatic-$\underline{H}$) 1 H, 7.10 (d) (aromatic-$\underline{H}$) 1 H, 7.70 (dd) (aromatic-$\underline{H}$) 1 H, 8.47 (d) (aromatic-$\underline{H}$) 2 H, 8.67 (s) (aromatic-$\underline{H}$) 1 H ppm. |
|---|---|

EXAMPLE 9

Production of 2-(pyridyl-3-methylsulfinyl)-pyrimidine hydrochloride 18.1 g (0.11 mole) of m-chloroperbenzoic acid dissolved in 300 ml of methylene chloride are added dropwise in 10–15 minutes at room temperature to a solution of 20.3 g (0.1 mole) of 2-(pyridyl-3-methylthio)-pyrimidine in 500 ml of methylene chloride. After a reaction time of 15 minutes, 120 ml of a 3% sodium hydrogen carbonate solution are added to the reaction solution and the methylene chloride phase is separated off. The organic phase is washed with water until neutral, dried over sodium sulfate and concentrated in vacuo. 200 ml of an equimolar solution of HCl in ethanol are added to the base accumulating, after which the hydrochloride is precipitated with ether. The 2-(pyridyl-3-methylsulfinyl)-pyrimidine hydrochloride is recrystallized from isopropanol.

Colorless crystals melting at 168–169° C.
Rf = 0.27 (CH$_2$Cl$_2$/MeOH 95:5 NH$_3$-vapors)
Yield: 8.2 g (32%)

| C$_{10}$H$_{10}$ClN$_3$OS (256) | Calculated: C 46.97 H 3.94 N 16.43 |
|---|---|
| | Observed: C 46.91 H 3.97 N 16.25 |
| $^1$H-NMR-data: (d$_4$-MeOH, TMS as internal standard | δ = 4.83 (dd) (SO—C$\underline{H}_2$) 2 H 7.53–9.27 (m) (aromatic-$\underline{H}$) 7 H ppm. |

EXAMPLE 10

Production of 2-(pyridyl-4-methylsulfinyl)-pyrimidine hydrochloride

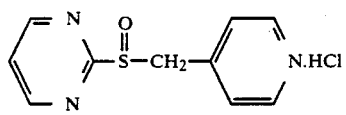

This compound is produced as in Example 9 from 2-(pyridyl-4-methylthio)-pyrimidine and m-chloroperbenzoic acid.

Colorless crystals melting at 165-166° C.
Rf = 0.20 (CH$_2$Cl$_2$/MeOH 95:5 NH$_3$-vapors)
Yield: 7.65 g (30%)
C$_{10}$H$_{10}$ClN$_3$OS (256)

| $^1$H-NMR-data: (d$_6$-DMSO, TMS) as internal standard) | $\delta$ = 4.80 (dd) (SO—C$\underline{H}_2$) 2 H, 7.73 (m) (aromatic-$\underline{H}$) 1 H, 8.83 (d) (aromatic-$\underline{H}$) 2 H, 9.00 (d) (aromatic-$\underline{H}$) 2 $\underline{H}$ ppm. |
|---|---|

EXAMPLE 11

Production of 4-methyl-2-(pyridyl-3-methylsulfinyl)-pyrimidine oxalate

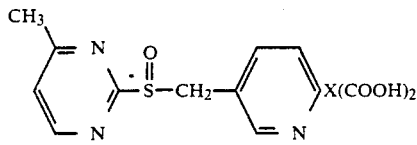

This compound is produced as in Example 9 from 3-methyl-2-mercaptopyrimidine and m-chloroperbenzoic acid.

Colorless crylstals metling at 132-134° C.
Rf = 0.81 (CH$_2$Cl$_2$/MeOH 8:2 NH$_3$-vapors)
Yield: 11.3 g (35%)
C$_{13}$H$_{13}$N$_3$O$_5$S (323)

| $^1$H-NMR-data: (d$_6$-DMSO, TMS as internal standard) | $\delta$ = 2.53 (s) (—C$\underline{H}_3$) 3 H, 4.43 (dd) (SO—C$\underline{H}_2$) 2 H, 7.17-7.67 (m) (aromatic-$\underline{H}$) 3 H, 8.00-8.67 (m) (aromatic-$\underline{H}$) 2 H, 8.77 (d) (aromatic-$\underline{H}$) 1 $\underline{H}$ ppm. |
|---|---|

EXAMPLE 12

Production of 2-(3-methylthio-1-methylpyridinium)-pyrimidine iodide

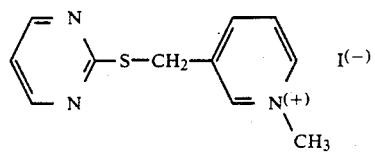

14.2 g (0.1 mole) of methyl iodide are added to a solution ob 20.3 g (0.1 mole) of 2-(pyridyl-3-methylthio)-pyrimidine in 250 ml of acetone and left to react for 1 hour at reflux temperature. The reaction solution is then concentrated in vacuo to dryness and the pale yellow solid accumulating is recrystallized from isopropanol.

Pale yellow solid melting at 104-105° C.
Rf = 0.38 (CH$_2$Cl$_2$/MeOH 8:2 NH$_3$-vapors)
Yield: 30.0 g (87%)
C$_{11}$H$_{12}$IN$_3$S (345)

Calculated: C 38.27 H 3.50 N 12.17
Observed: C 38.44 H 3.49 N 12.16

| $^1$H-NMR-data: (d$_4$-MeOH, TMS as internal standard) | $\delta$ = 4.67 (s) (S—C$\underline{H}_2$) 2 H, 7.20 (t) (aromatic-$\underline{H}$) 1 H, 8.13 (dd) (aromatic-$\underline{H}$) 1 H, 8.57-9.0 (m) (aromatic-$\underline{H}$) 4 H, 9.30 (s) (aromatic-$\underline{H}$) 1 $\underline{H}$ ppm. |
|---|---|

EXAMPLE 13

Production of 2-(3-methylthio-1-ethylpyridinium)-pyrimidine iodide

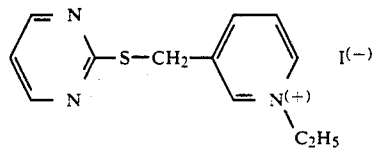

This compound is produced as in Example 12 from 2-(pyridyl-3-methylthio)-pyrimidine and ethyl iodide.

Pale yellow solid melting at 137-138° C.
Rf = (CH$_2$Cl$_2$/MeOH 8:2)
Yield: 24.0 g (67%)
C$_{12}$H$_{14}$IN$_3$S (359)

Calculated: C 40.12 H 3.93 N 11.70
Observed: C 40.12 H 3.97 N 11.76

| $^1$H-NMR-data: (d$_6$-DMSO, TMS) as internal standard) | $\delta$ = 1.60 (t) (C$\underline{H}_3$—CH$_2$—) 3 H, 4.67 (s) (S—C$\underline{H}_2$) 2 H, 4.73 (q) (C$\underline{H}_2$—CH$_3$) 2 H, 7.33 (t) (aromatic-$\underline{H}$) 1 H, 8.20 (dd) (aromatic-$\underline{H}$) 1 H, 8.80 (m) (aromatic-$\underline{H}$) 3 H, 9.10 (d) (aromatic-$\underline{H}$) 1 H, 9.40 (s) (aromatic-$\underline{H}$) 1 H ppm. |
|---|---|

EXAMPLE 14

Production of soft gelatin capsultes containing the active principle according to the invention
Composition:

| e.g. Compound according to the invention Example 12 | 100.0 mg |
|---|---|
| Rapeseed oil | 281.0 mg |
| Beeswax | 2.0 mg |
| Partially hydrogenated vegetable oil | 8.0 mg |
| Soya lecithin | 8.0 mg |
| 3-Ethoxy-4-hydroxy benzaldehyde | 1.0 mg |
| | 400.0 mg |

The ingredients are mixed, homogenized and made up into soft gelatin capsultes in the usual way.

EXAMPLE 15

Production of dosing aerosol containing the active principle according to the invention Composition:

| e.g. Compound according to the invention Example 12 | 10.0 mg |
|---|---|
| Sorbitan trioleate | 0.5 mg |
| Difluoromethane | 35.5 mg |
| Dichlorotetrafluoroethane | 25.0 mg |

-continued

| | |
|---|---|
| Total dose per spray | 71.0 mg |

The ingredients are dissolved cold and 10 g of the resulting solution are introduced into a suitable pressurized gas pack.

EXAMPLE 16

Production of ampoules containing the active principle according to the invention Composition:

| | |
|---|---|
| e.g. Compound according to the invention Example 12 | 100.0 mg |
| Polyethylene glycol 300 | 630.0 mg |
| 1,2-Propane diol | 735.0 mg |
| α-Tocopherol | 1.0 mg |
| Disodium hydrogen phosphate | 4.0 mg |
| Sodium dihydrogen phosphate | 20.0 mg |
| Water for injection purposes | 610.0 mg |
| Total weight of contents | 2100.0 mg |

The ingredients are dissolved and the resulting solution is made up into 2 ml ampoules.

We claim:

1. A pyrimidine-thioalkyl pyridine compound having the formula

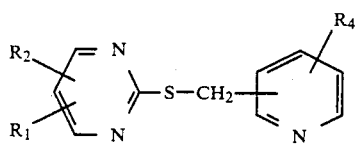

or the formula

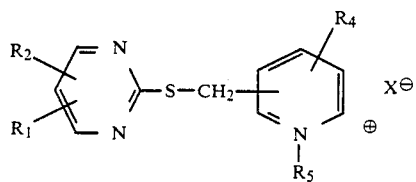

wherein $R_1$, $R_2$ and $R_4$ are the same or different and are selected from the group consisting of hydrogen, lower alkyl, halogen, amino and hydroxy with the proviso that at least one of $R_1$ or $R_2$ is amino or hydroxy, $R_5$ is a lower alkyl group, X is a halogen atom, the pyrimidine-thioalkyl group being bonded in the 2-, 3- or 4-position of the pyridine ring, or a pharmaceutically acceptable salt thereof.

2. A pyrimidine-thioalkyl pyridine compound having the formula

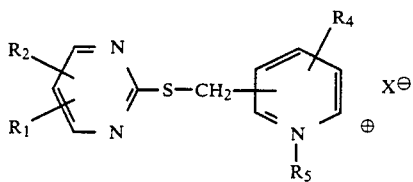

wherein $R_1$, $R_2$ and $R_4$ are the same or different and are selected from the group consisting of hydrogen, lower alkyl, halogen, amino and hydroxy, $R_5$ is a lower alkyl group, X is a halogen atom, the pyrimidine-thioalkyl group being bonded in the 2-, 3- or 4-position of the pyridine ring.

3. A pyrimidine-thioalkyl pyridine compound having either the formula:

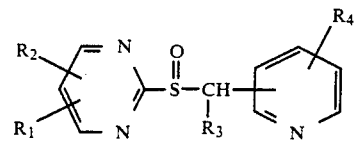

or the formula:

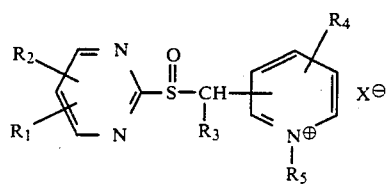

wherein $R_1$ to $R_4$ may be the same or different and represent hydrogen, lower alkyl, halogen, amino or hydroxy groups, $R_5$ is a lower alkyl group, X is a halogen atom, the pyrimidinethioalkyl group being bonded in the 2-, 3- or 4-position of the pyridine ring, or a pharmaceutically acceptable salt thereof.

4. A bronchosecretolytic or mucolytic composition of matter, comprising (i) a bronchosecretolytically or mucolytically effective amount of a pyrimidine-thioalkyl pyridine compound as defined in claim 3, or a pharmaceutically acceptable salt thereof, and (ii) a pharmaceutically acceptable carrier or diluent thereof.

5. A method for eliciting a bronchosecretolytic or mucolytic response in a mammalian organism in need of such treatment, comprising administering to such organism a bronchosecretolytically or mucolytically effective amount of a pyrimidine-thioalkyl pyridine compound as defined by claim 3, or a pharmaceutically acceptable salt thereof.

6. A method according to claim 5, wherein said method includes administration of said pyrimidine-thioalkyl pyridine compound in oral dosage form.

7. A method as claimed in claim 5, wherein said method includes parental administration of said pyrimidine-thioalkyl pyridine compound.

8. A method for reducing the viscosity of sputum in a mammalian organism in need of such treatment, comprising administering to such organism a bronchosecretolytically or mucolytically effective amount of a pyrimidine-thioalkyl pyridine compound as defined in claim 3, or a pharmaceutically acceptable salt thereof.

9. A method for treating acute or chronic respiratory disease in a mammalian organism in need of such treatment, comprising administering to such organism a therapeutically effective amount of a pyrimidine-thioalkyl pyridine compound as defined in claim 3, or a pharmaceutically acceptable salt thereof.

10. A method for treating bronchial illness in a mammalian organism, comprising administering to such organism a therapeutically effective amount of a pyrimidine-thioalkyl pyridine compound as defined in claim 3, or a pharmaceutically acceptable salt thereof.

11. A compound as claimed in claim 1, having the formula:

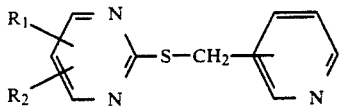

wherein $R_1$ and $R_2$ are bonded to the pyrimidine ring in the 3-, 4- or 5- position.

12. A compound as claimed in claim 4, wherein $R_3$ is a lower alkyl group and $R_4$ is hydrogen atom or a lower alkyl group.

13. A compound as claimed in claim 3, having the formula:

14. A compound as claimed in claim 4, having the formula:

15. A compound as claimed in claim 1, wherein said compound is 4-amino-2-(pyridyl-3-methylthio)-pyrimidine.

16. A compound as claimed in claim 1, wherein said compound is 4-hydroxy-2-(pyridyl-3-methylthio)-pyrimidine.

17. A compound as claimed in claim 1, wherein said compound is 4-amino-6-hydroxy-2-(pyridyl-3-methylthio)-pyrimidine.

18. A compound as claimed in claim 1, wherein said compound is 4,6-diamino-2- (pyridyl-3-methylthio)-pyrimidine succinate.

19. A compound as claimed in claim 1, wherein said compound is 4-hydroxy-6-methyl-2-(pyridyl)-3-methylthio)-pyrimidine.

20. A compound as claimed in claim 1, wherein said compound is 4-amino-2-hydroxy-2-(pyridyl-6-chloro-1-methylthio)-pyrimidine.

21. A compound as claimed in claim 3, wherein said compound is 2-(pyridyl-3-methylsulfinyl)-pyrimidinehydro chloride.

22. A compound as claimed in claim 3, wherein said compound is 2-(pyridyl-4-methylsulfinyl)-pyrimidine hydrochloride.

23. A compound as claimed in claim 3, wherein said compound is 4-methyl-2-(pyridyl-3-methylsulfinyl)-pyrimidine oxalate.

24. A compound as claimed in claim 2, wherein said compound is 2-(3-methylthio-1-methylpyridinium)-pyrimidine iodide.

25. A compound as claimed in claim 2, wherein said compound is 2-(3-methylthio-1-ethylpyridinium)-pyrimidine iodide.

26. A method for eliciting a bronchosecretolytic or mucolytic response in a mammalian organism in need of such treatment, comprising administering to such organism a bronchosecretolytically or mucolytically effective amount of a pyrimidine-thioalkyl pyridine compound as defined by claim 1, or a pharmaceutically effective salt thereof.

27. A method according to claim 28, wherein said method includes administration of said pyrimidine-thioalkyl pyridine compound in oral dosage form.

28. A method as claimed in claim 28, wherein said method includes parenteral administration of said pyrimidine-thioalkyl pyridine compound.

29. A method for reducing the viscosity of sputum in a mammalian organism in need of such treatment, comprising administering to such organism a bronchosecretolytically or mucolytically effective amount of a pyrimidine-thioalkyl pyridine compound as defined in claim 1, or a pharmaceutically effective salt thereof.

30. A method for treating acute or chronic respiratory disease in a mammalian organism in need of such treatment, comprising administering to such organism a therapeutically effective amount of a pyrimidine-thioalkyl pyridine compound as defined in claim 1, or a pharmaceutically effective salt thereof.

31. A method for treating bronchial illness in a mammalian organism, comprising administering to such organism a therapeutically effective amount of a pyrimidine-thioalkyl pyridine compound as defined in claim 1, or a pharmaceutically effective salt thereof.

32. A bronchosecretolytic or mucolytic composition of matter, comprising (i) a bronchosectetolytically or mucoltyically effective amount of a pyrimidine-thioalkyl pyridine compound as defined in claim 1, or a pharmaceutically effective salt thereof, and (ii) a pharmaceutically acceptable carrier or diluent thereof.

* * * * *